US006949379B2

(12) United States Patent
Ramachandra

(10) Patent No.: US 6,949,379 B2
(45) Date of Patent: Sep. 27, 2005

(54) APTAMER-MEDIATED REGULATION OF GENE EXPRESSION

(75) Inventor: Murali Ramachandra, San Diego, CA (US)

(73) Assignee: Canji, Inc., San Diego, CA (US)

( * ) Notice: Subject to any disclaimer, the term of this patent is extended or adjusted under 35 U.S.C. 154(b) by 129 days.

(21) Appl. No.: 10/036,091

(22) Filed: Oct. 19, 2001

(65) Prior Publication Data

US 2002/0115629 A1 Aug. 22, 2002

Related U.S. Application Data

(60) Provisional application No. 60/242,106, filed on Oct. 20, 2000.

(51) Int. Cl.[7] ................. C12N 15/63; C12N 15/85; C12N 1/21; C12N 1/19; C12N 15/11
(52) U.S. Cl. ................. 435/320.1; 435/325; 435/252.3; 435/254.2; 435/254.11; 435/419; 536/23.1; 536/23.4; 536/24.1; 536/24.5; 536/24.33
(58) Field of Search ................. 536/23.1, 23.4, 536/24.1, 24.5, 24.33; 435/320.1, 325, 252.3, 254.2, 254.11, 419

(56) References Cited

U.S. PATENT DOCUMENTS 5,756,291 A 5/1998 Griffin et al.
5,795,721 A 8/1998 Rabin et al.
5,874,534 A 2/1999 Vegeto et al.

(Continued)

FOREIGN PATENT DOCUMENTS

WO WO 98/29430 A1 7/1998
WO WO 99/04800 A1 2/1999
WO WO 99/13077 A2 3/1999

(Continued)

OTHER PUBLICATIONS

Perrem et al. Oncogene. Oct. 5, 1995;11(7):1299–307.*
Wolffe et al. Vitamins and Hormones. Jan. 2000; 58:449–92.*
Yao et al. Human Gene Therapy. 1998; 9:1939–50.*
Jayasena, SD. Clin. Chem. 1999; 45(9):1628–50.*
Check, E. Nature, 2003, 421: 678.*
Juengst, ET. BMJ, 2003, 326: 1410–11.*
Jayasena, S. Clinical Chemistry, Sep. 1999, 45(9): 1628–50.*
Werstuck and Green, Science, Oct. 1998, 282:296–8.*
Yamamoto et al. Genes to Cells, 2000, 5:371–87.*
Dohjima et al., *British Journal of Cancer*, 82(*1*):16–19 (2000).
Fan et al., *Molecular Endocrinology*, 11(*9*):1342–1352 (1997).
Grate et al., *Biorganic and Medicinal Chemistry*, 9(*10*):2565–2570 (2001).
Blind et al., *Proc. Natl. Acad. Sci.*, 96:3606–3610 (1999).
Boyd, "Tiny Switch Shuts Down Genes," *Science, Daily inScight*, Posted Oct. 9, 1998.

(Continued)

*Primary Examiner*—Gerry Leffers
*Assistant Examiner*—Ramin Akhavan
(74) *Attorney, Agent, or Firm*—Townsend and Townsend and Crew LLP

(57) ABSTRACT

This invention provides methods of regulating gene expression. An aptamer is positioned in a nucleic acid molecule along with a sequence encoding a transcriptional regulatory polypeptide. The aptamer disrupts translation of the transcriptional regulatory polypeptide when contacted with an aptamer-binding ligand. Gene expression levels can be either increased or decreased by the disclosed methods, depending on whether the transcriptional regulatory polypeptide is a repressor or activator, and the degree of the effect is dependent upon the dose of the ligand. Nucleic acid molecules, expression cassettes, expression vectors and cells useful in the gene regulation methods are also provided.

28 Claims, 1 Drawing Sheet

U.S. PATENT DOCUMENTS

| | | | |
|---|---|---|---|
| 5,882,941 A | | 3/1999 | Essigmann et al. |
| 5,968,793 A | * | 10/1999 | Liu et al. .................... 800/260 |
| 2002/0006661 A1 | * | 1/2002 | Green et al. ................ 435/325 |

FOREIGN PATENT DOCUMENTS

| | | |
|---|---|---|
| WO | WO 00/20040 A1 | 4/2000 |
| WO | WO 00/24912 A1 | 5/2000 |
| WO | WO 00/26226 A1 | 5/2000 |
| WO | WO 00/39318 A1 | 7/2000 |
| WO | WO 01/64956 A2 | 9/2001 |

OTHER PUBLICATIONS

Eaton, *Curr. Opin. Chem. Biol., 1*:10–16 (1997).
Ellington et al., *Nature, 346*:818 (1990).
Famulok, *Curr. Opin. Struct. Biol., 9*:324–329 (1999).
Hermann et al., *Science, 287*:820–825 (2000).
Ohkawa et al., *Human Gene Therapy, 11*:577–585 (2000).
Osborne et al., *Curr. Opin. Chem. Biol., 1*:5–9 (1997).
Tuerk et al., *Science, 249*:505 (1990).
Werstuck et al., *Science, 282*:296–298 (1998).

* cited by examiner

APTAMER-MEDIATED REGULATION OF GENE EXPRESSION

CROSS-REFERENCE TO RELATED APPLICATION

This application claims the benefit of U.S. Provisional Application No. 60/242,106, filed Oct. 20, 2000, which application is incorporated herein by reference for all purposes.

FIELD OF THE INVENTION

This invention pertains to the field of gene regulation. In particular, the invention pertains to the use of aptamers to control translation of transcriptional regulatory polypeptides.

BACKGROUND OF THE INVENTION

The search for therapeutics is largely focused on the regulation of gene expression and the inactivation of gene products. The development of in vitro selection techniques for identifying aptamer sequences that specifically bind a desired target molecule has provided new opportunities for the manipulation of biological interactions. Aptamers are nucleic acid molecules that are capable of binding to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. For recent reviews of aptamers and their ligands, see Eaton, Curr. Opin. Chem. Biol. 1:10–16 (1997), Famulok, Curr. Opin. Struct. Biol. 9:324–9(1999), and Hermann and Patel, Science 287:820–5 (2000). A variety of approaches have been taken which make use of aptamer sequences in an attempt to alter the behavior and/or populations of biomolecules within cells.

In the most common approach to date, aptamers have been used to disrupt the molecular interactions of the end products of gene expression—proteins. Thus, aptamers have been selected which bind various protein targets and disrupt the interactions of those proteins with other proteins and/or disrupt catalysis by the protein targets. For instance, Blind et al. have shown that an RNA aptamer which specifically binds β2 integrin LFA-1 can shut down a signaling pathway in vivo (Blind et al., Proc. Natl. Acad. Sci. 96:3606–3610 (1999)). As another example, U.S. Pat. No. 5,756,291 discloses DNA aptamers which bind thrombin and inhibit coagulation. For a review of the success of the use of aptamers as therapeutic reagents, see Osborne et al., Curr. Opin. Chem. Biol. 1:5–9 (1997). Such approaches directed towards the protein products of genes, however, are not very efficient in addressing diseases or conditions where an aberrant amount of a protein is expressed and may be useless in the treatment of diseases or conditions where a protein is underexpressed.

In another approach, and one more directed towards modifying gene expression, aptamers have been used to prevent transcription of a gene by specifically binding the DNA-binding sites of regulatory proteins. In this manner, the aptamers effectively compete with the binding sites on the gene for interaction with the regulatory protein. For instance, PCT Publication No. WO 98/29430 teaches modulation of the immune response. In the taught method, aptamers are used to bind the DNA- binding sites of Sp1 and Sp1-related proteins. However, because the binding of the aptamer to the DNA is a competitive process, high levels of active aptamers are required in vivo to achieve reasonable efficiency of gene modulation.

In yet another approach, the PCT Publication No. WO 00/20040 discloses the inhibition of expression of a gene in a cell by contacting a small molecule with an aptamer in the 5'untranslated region (5'UTR) of the gene's mRNA transcript. The binding of the small molecule to the aptamer results in disruption of the translation of the mRNA, leading to a change in gene expression. However, the disclosed technique is limited in that it can only be used to turn off the expression of a gene, not activate it. Furthermore, the degree of downregulation will merely be proportional to the amount of the aptamer's ligand which has been administered to the cell.

Thus, the methods that use aptamers in therapeutics which have been developed to date have not fully addressed the need for methods of efficiently upregulating and downregulating gene expression in a cell in a dose-responsive manner.

SUMMARY OF THE INVENTION

The present invention provides methods of regulating gene expression that, unlike many known methods for regulating gene expression, are dose-responsive and can facilitate either upregulation or downregulation of transgenes and endogenous genes.

In one embodiment of the invention, the method of controlling expression of a gene involves contacting an aptamer-binding ligand with an mRNA that comprises an aptamer and a polynucleotide that encodes a transcriptional regulatory polypeptide, where the transcriptional regulatory polypeptide regulates expression of the gene. In this method, the ligand binds to the aptamer and thereby inhibits translation of the transcriptional regulatory polypeptide, resulting in a change in the expression level of the gene.

In another embodiment, the invention provides a method of retarding undesirable cell proliferation. This method involves administering to undesirably proliferating cells a nucleic acid construct that comprises a promoter operably linked to a polynucleotide, which, when transcribed, yields an mRNA that comprises both an aptamer and a polynucleotide sequence encoding a transcriptional regulatory polypeptide that regulates expression of a gene involved in the regulation of cell proliferation. The method also involves the administration of a ligand that binds to the aptamer. The binding of the ligand to the aptamer inhibits translation of the transcriptional regulatory polypeptide, thus causing a change in the expression level of the gene, which, in turn, ameliorates the undesirable cell proliferation.

Also provided by the invention is a nucleic acid molecule comprising an aptamer and a polynucleotide that encodes a transcriptional regulatory polypeptide, where the binding of a ligand to the aptamer inhibits translation of the transcriptional regulatory polypeptide. Expression cassettes and expression vectors that comprise a promoter operably linked to a polynucleotide from which is transcribed a nucleic acid molecule of the invention are also provided. Cells that comprise the nucleic acids molecules of the invention are likewise provided.

DETAILED DESCRIPTION OF THE INVENTION

Definitions

Figure 1:
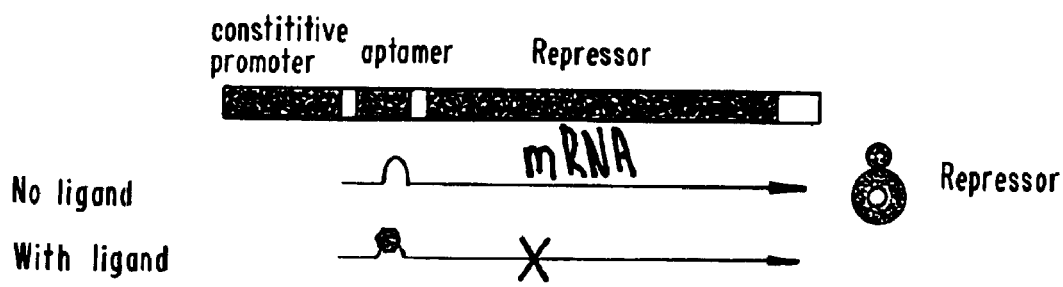
FIG. 1 shows a schematic representation of a method of controlling expression of a gene using the nucleic acids of the present invention. In the figure, the transcriptional regulatory polypeptide is a repressor. Upon binding of the ligand to the aptamer, translation of the repressor, i.e., mRNA, is blocked and the repression of the therapeutic gene is relieved.
Figure 1:
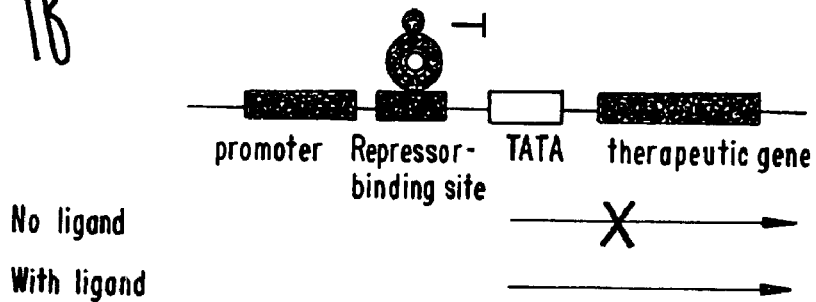

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

An "aptamer" refers to a nucleic acid molecule that is capable of binding to a particular molecule of interest with high affinity and specificity (Tuerk and Gold, *Science* 249:505 (1990); Ellington and Szostak, *Nature* 346:818 (1990)). The binding of a ligand to an aptamer, which is typically RNA, changes the conformation of the aptamer and the nucleic acid within which the aptamer is located. The conformation change inhibits translation of an mRNA in which the aptamer is located, for example, or otherwise interferes with the normal activity of the nucleic acid. Aptamers may also be composed of DNA or may comprise non-natural nucleotides and nucleotide analogs. An aptamer will most typically have been obtained by in vitro selection for binding of a target molecule. However, in vivo selection of an aptamer is also possible.

Aptamers have specific binding regions which are capable of forming complexes with an intended target molecule in an environment wherein other substances in the same environment are not complexed to the nucleic acid. The specificity of the binding is defined in terms of the comparative dissociation constants (Kd) of the aptamer for its ligand as compared to the dissociation constant of the aptamer for other materials in the enviromnent or unrelated molecules in general. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least about 100-fold less, and most preferably at least about 200-fold less.

An aptamer will typically be between about 10 and about 300 nucleotides in length. More commonly, an aptamer will be between about 30 and about 100 nucleotides in length.

A "small organic molecule" is a carbon-containing molecule which is typically less than about 2000 daltons. More typically, the small organic molecule is a carbon-containing molecule of less than about 1000 daltons. The small organic molecule may or may not be a biomolecule with known biological activity.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Cassol et al. (1992); Rossolini et al., *Mol. Cell. Probes* 8:91–98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

The term "gene" is used broadly to refer to any segment of DNA associated with a biological function. Thus, genes include coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

An "exogenous DNA" or a "transgene," refers to a gene that originates from a source foreign to the particular host cell, or, if from the same source, is modified from its original form. Thus, a transgene in a host cell includes a gene that is endogenous to the particular host cell, but has been modified in some manner. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "naturally-occurring" is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

A DNA segment is "operably linked" when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers, for example, need not be contiguous with the coding sequences whose transcription they control. Linking is accomplished by ligation at convenient restriction sites or at adapters or linkers inserted in lieu thereof.

"Promoter" refers to a region of DNA involved in binding the RNA polymerase to initiate transcription. An "inducible promote" refers to a promoter that directs expression of a gene where the level of expression is alterable by environmental or developmental factors such as, for example, temperature, pH, transcription factors and chemicals. The term "constitutive promoter" refers to a promoter that is active under most environmental and developmental conditions.

An "expression cassette" is a nucleic acid construct, generated recombinantly or synthetically, with nucleic acid elements that are capable of effecting expression of a gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "vector" refers to a composition for transferring a nucleic acid (or nucleic acids) to a host cell. A vector comprises a nucleic acid encoding the nucleic acid to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

The term "viral vector" refers to a vector that comprises a viral nucleic acid and can also include a viral capsid and/or replication function.

The term "expression vector" refers to a vector which comprises some or all of the following elements operably linked at appropriate distance for allowing functional gene expression: replication origin, promoter, enhancer, 5' mRNA leader sequence, ribosomal binding site, nucleic acid cassette, selectable marker sequences, and termination and polyadenylation sites. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An expression vector is constructed so that the particular coding sequence is located in the vector with the appropriate regulatory sequences, the positioning and orientation of the coding sequence with respect to the control sequence being such that the coding sequence is transcribed under the "control" of the control sequence. Modification of the sequences encoding the particular protein of interest may be desirable to achieve this end. For example, in some cases it may be necessary to modify the sequence so that it may be attached to the control sequences with the appropriate orientation, or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

"transcriptional regulatory polypeptide" refers to a protein or effector domain of protein that has the ability to modulate transcription. A transcriptional regulatory polypeptide may act as either a transcriptional activator, a transcriptional repressor, or in some rare cases, as either. Transcriptional regulatory polypeptides include, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g., Utley et al., Nature 394:498–502 (1998)).

The term "physiological conditions" refers to the salt concentration and ionic strength in an aqueous solution which characterize fluids found in human metabolism commonly referred to as physiological buffer or physiological saline. In general, these are represented by an intracellular pH of 7.1 and salt concentrations of 3–15 mM $Na^+$, 140 mM $K^+$, 6.3 mM $Mg^{+2}$, $10^{-4}$ mM $Ca^{+2}$, 3–15 mM $Cl^-$, and an extracellular pH of 7.4 and salt concentrations of 145 mM $Na^+$, 3 mM $K^+$, 1–2 mM $Mg^{+2}$, 1–2 mM $Ca^{+2}$, 110 mM $Cl^-$

DESCRIPTION OF THE PREFERRED EMBODIMENTS

The invention provides methods for activating expression of a gene through the presence of an aptamer-binding ligand. The methods involve contacting with the ligand an mRNA that includes an aptamer and a polynucleotide that encodes a transcriptional regulatory polypeptide that regulates expression of the gene of interest. The ligand binds to the aptamer, thus inhibiting translation of the transcriptional regulatory polypeptide and resulting in a change in the expression level of the gene of interest. Also provided are nucleic acid molecules that include both an aptamer and a polynucleotide that encodes a transcriptional regulatory peptide.

The gene regulation methods of the invention provide significant advantages over previously known methods for modulating gene expression. The use of an aptamer-regulatory polypeptide-encoding construct precludes the need to modify a gene already in a cell to, for example, replace a native promoter with an inducible promoter that is responsive to a desired stimulus. Instead, one can introduce into a cell a vector that expresses the aptamer-regulatory polypeptide-encoding nucleic acid. Expression of endogenous genes that are regulated by the regulatory polypeptide are then subject to modulation based on the presence or absence of the ligand for the aptamer. Thus, the methods can be used not only to control expression of genes that are introduced into a cell, but also genes that are native to the cell.

Another advantage provided by the methods and constructs of the invention is that the degree to which gene expression is modulated is dose-responsive. Thus, the methods of the invention allow the level of expression to be titrated based on the amount of the aptamer ligand that is present in the cells. In contrast, most inducible or repressible systems for gene expression are either on or off.

Yet another advantage of the instant invention is that the expression of a gene of interest can be induced in response to a wide range of molecules. For example, one can use an aptamer that binds to a protein, a metal ion, an organic molecule, and the like. The ligand can be a molecule that is present in a cell due to a disease state, or can be a molecule that is introduced into a cell, for example, in conjunction with introduction of the aptamer-regulatory polypeptide-encoding nucleic acid.

A. Nucleic Acids That Include an Aptamer and a Regulatory Polypeptide Coding Region The invention provides nucleic acids (e.g., mRNA molecules) that include an aptamer as well as a coding region for a regulatory polypeptide. The aptamer is positioned in the nucleic acid molecule such that binding of a ligand to the aptamer prevents translation of the regulatory polypeptide.

In some presently preferred embodiments, the aptamer is located in the 5' untranslated region of the nucleic acid molecule.

In other preferred embodiments of the invention, the nucleic acid molecule is an RNA molecule. Most preferably, the nucleic acid molecule is an mRNA transcript.

1. Aptamers and Ligands

Aptamers are readily made that bind to a wide variety of molecules. Each of these molecules can be used as a modulator of gene expression using the methods of the invention. For example, organic molecules, nucleotides, amino acids, polypeptides, target features on cell surfaces, metal ions, saccharides, have all been shown to be suitable for isolating aptamers that can specifically bind to the respective ligand. For instance, organic dyes such as Hoechst 33258 have been successfully used as target ligands in vitro aptamer selections (Werstuck and Green, *Science* 282:296–298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, *Science* 9:324–9 (1999).

In a preferred embodiment, the ligand of the aptamer of the nucleic acid molecule of the invention is a cell-permeable, small organic molecule. Small organic molecules which do not have a general inhibitory effect on translation are preferred as ligands. The small molecule preferably also exhibits in vivo persistence sufficient for achieving the desired level of inhibition of translation. The molecules also can be screened to identify those that are bioavailable after, for example, oral administration. In a preferred embodiment of the invention, the ligand is non-toxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition.

Thus, the ligand for an aptamer is optionally an antibiotic, such as chloramphenicol. In an alternative embodiment, the ligand of the aptamer is an organic dye such as Hoescht dye 33258. In still another embodiment, the ligand may be a metal ion.

The aptamer of the nucleic acid of the invention can be comprised entirely of RNA. In other embodiments of the invention, however, the aptamer can instead be comprised entirely of DNA, or partially of DNA, or partially of other nucleotide analogs. To specifically inhibit translation in vivo, RNA aptamers are preferred. Such RNA aptamers are preferably introduced into a cell as a DNA that encodes the aptamer sequence such that transcription results in the RNA aptamer. Alternatively, an RNA aptamer itself can be introduced into a cell.

Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak, *Nature* 346:818 (1990), Tuerk and Gold, *Science* 249:505 (1990), U.S. Pat. No. 5,582,981, PCT Publication No. WO 00/20040, U.S. Pat. No. 5,270,163, Lorsch and Szostak, *Biochemistry*, 33:973 (1994), Mannironi et al., *Biochemistry* 36:9726 (1997), Blind, *Proc. Nat'l. Acad. Sci. USA* 96:3606–3610 (1999), Huizenga and Szostak, *Biochemistry*, 34:656–665 (1995), PCT Publication Nos. WO 99/54506, WO 99/27133, WO 97/42317 and U.S. Pat. No. 5,756,291.

Generally, in their most basic form, in vitro selection techniques for identifying RNA aptamers involve first preparing a large pool of DNA molecules of the desired length that contain at least some region that is randomized or mutagenized. For instance, a common oligonucleotide pool for aptamer selection might contain a region of 20–100 randomized nucleotides flanked on both ends by an about 15–25 nucleotide long region of defined sequence useful for the binding of PCR primers. The oligonucleotide pool is amplified using standard PCR techniques. The DNA pool is then transcribed in vitro. The RNA transcripts are then subjected to affinity chromatography. The transcripts are most typically passed through a column or contacted with magnetic beads or the like on which the target ligand has been immobilized. RNA molecules in the pool which bind to the ligand are retained on the column or bead, while non-binding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand.

For use in the present invention, the aptamer is preferably selected for ligand binding in the presence of salt concentrations and temperatures which mimic normal physiological conditions.

Once an aptamer sequence has been successfully identified, the aptamer may be further optimized by performing additional rounds of selection starting from a pool of oligonucleotides comprising the mutagenized aptamer sequence.

One can generally choose a suitable ligand without reference to whether an aptamer is yet available. In most cases, an aptamer can be obtained which binds the small, organic molecule of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong and the structure formed by the aptamer when bound to its ligand must be significant enough so as to disrupt translation of the attached transcript. The structure of the aptamer in the absence of the ligand, on the other hand, should be minimal. Whether or not an aptamer meets these criteria can be readily determined by one of ordinary skill in the art. For instance, a chosen aptamer could be inserted in the 5'-UTR of a reporter gene on an expression vector. In the absence of the aptamer's ligand, cells transfected with the expression vector should show expression of the reporter gene. Once the aptamer is added, however, the expression should cease if the aptamer of the mRNA is effective in blocking translation. One of ordinary skill in the art will recognize that effective conditional expression of a reporter gene could be determined in any of a number of cells or animal models and using a number of different available reporter genes such as genes encoding green fluorescent protein (GFP), yellow fluorescent protein (YFP), and blue fluorescent protein (BFP). Other suitable marker genes include the thymidine kinase (tk), dihydrofolate reductase (DHFR), chloramphenicol acetyltransferase (CAT), β-lactamase, β-galactosidase (β-gal), and aminoglycoside phosphotransferase (APH) genes.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue. Preferably, the required ligand concentration for in vivo use is also below that which could have undesired effects on the organism.

2. Regulatory Polypeptides

The nucleic acid molecules of the invention also comprise a polynucleotide that encodes a transcriptional regulatory polypeptide. The transcriptional regulatory polypeptide may be a transcriptional activator, coactivator, repressor, or corepressor.

In one embodiment, the transcriptional regulatory polypeptide encoded by the nucleic acid of the invention is a naturally-occurring polypeptide. However, in another embodiment of the invention, the encoded transcriptional regulatory polypeptide is recombinant and is engineered by fusing two or more domains derived from different proteins. Most typically, the different functional domains of the regulatory polypeptide will each have been derived from naturally-occurring polypeptides.

In a preferred embodiment of the invention, the transcriptional regulatory polypeptide encoded by the nucleic acid of the invention acts as a transcriptional repressor. In one embodiment, the transcriptional regulatory polypeptide is a known transcription factor. Alternatively, the transcriptional regulatory polypeptide may comprise a transcriptional repressor domain from a transcription factor. Optionally, the regulatory polypeptide may be a co-repressor. Possible transcriptional repressors or transcriptional repressor domains include, but are not limited to, those derived from the following transcription factors: Rb protein; v-erbA; retinoic acid receptor alpha; thyroid hormone receptor alpha; yeast Ssn6/Tup1 protein complex; SIR1; NeP1; TSF3; SFI; WT1; Oct-2.1; E4BP4; ZF5; human KOX-1 protein (Thiesen et al., *New Biologist* 2:363–374 (1990); Margolin et al., *PNAS* 91:4509–4513 (1994); Pengue et al., *Nucl. Acids Res.* 22:2908–2914 (1994); Witzgall et al., *PNAS* 91:4514–4518 (1994)); MAD (see, e.g., Sommer et al., *J. Biol. Chem.* 273:6632–6642 (1998); Guptaetal., *Oncogene* 16:1149–1159 (1998); Queva et al., *Oncogene* 16:967–977 (1998); Larsson et al., *Oncogene* 15:737–748 (1997); Laherty et al, *Cell* 89:349–356 (1997); and Cultraro et al., *Mol Cell. Biol.* 17:2353–2359 (1997)); FKHR (forkhead in rhapdosarcoma gene; Ginsberg et al, *Cancer Res.* 15:3542–3546 (1998); Epstein et al., *Mol. Cell. Biol.* 18:4118–4130 (1998)); EGR-1 (early growth response gene product-1; Yan et al., *PNAS* 95:8298–8303 (1998); and Liu et al., *Cancer Gene Ther.* 5:3–28 (1998)); the ets2 repressor factor repressor domain (ERD; Sgouras et al., *EMBO J.* 14:4781–4793 ((19095)); and the MAD smSIN3 interaction domain (SID; Ayer et al., *Mol. Cell. Biol.* 16:5772–5781 (1996)). A KRAB co-repressor, e.g., KAP-1, can also be used (Friedman et al, *Genes Dev.* 10:2067–2078 (1996)).

In an alternative embodiment of the invention, the transcriptional regulatory polypeptide encoded by the nucleic acid acts as a transcriptional activator. Thus, the regulatory polypeptide may optionally be a transcription factor that is an activator or may optionally comprise a transcriptional activator domain from a transcription factor. The transcriptional regulatory polypeptide may optionally be a co-activator. Possible activation domains suitable for use in the transcriptional regulatory polypeptide include, but are not limited to, the activation domains of the following proteins: HSV VP16 (see, e.g., Hagmann et al., *J. Virol.* 71:5952–5962 (1997)); VP64 (Seipel et al., *EMBO J.* 11:4961–4968 (1996)); nuclear hormone receptors (see, e.g., Torchia et al., *Curr. Opin. Cell. Biol.* 10:373–383 (1998)); the p65 subunit of nuclear factor kappa B (Bitko & Barik, *J. Virol.* 72:5610–5618 (1998) and Doyle & Hunt, *Neuroreport* 8:2937–2942 (1997)); and EGR-1 (early growth response gene product-1; Yan et al., *PNAS* 95:8298–8303 (1998); and Liu et al., *Cancer Gene Ther.* 5:3–28 (1998)).

Regardless of whether the encoded transcriptional regulatory polypeptide which acts as a repressor or an activator, the polypeptide may optionally comprise a DNA-binding domain, such as that of any of the following proteins: E2F-1; GAL4; a STAT protein (Barahmand-Pour et al., *Curr. Top. Microbiol. Immunol.* 211:121–8 (1996)); a steroid/thyroid receptor protein; a tetracycline repressor (tetR); CTF/NF1; CP family; C/EBP family (Wedel et al., *Immunobiology* 193:171–85 (1995)); Sp1; Oct1; Oct2; HSF; SRF; GATA transcription factors (Simon, *Nat. Genet.* 11:9–11 (1995); Weiss et al., *Exp. Hematol.* 23:99–107); Pit-1; MyoD1; NF-kB; and NRSF/REST.

Zinc finger DNA binding motifs (e.g., a modular Cys2-His2 zinc finger DNA binding motif) are also suitable for use in the invention. Through modification of these motifs, one can obtain proteins that have DNA binding specificity that is tailored for a particular desired application (see, e.g., Beerli et al., *Proc. Nat'l. Acad. Sci. USA* 97:1495–1500 (2000); Beerli et al., *J. Biol. Chem.* 275:32617–32627 (2000); Segal et al., *Proc. Nat'l. Acad. Sci. USA* 96:2758–2763 (1999); and Beerli et al., *Proc. Nat'l. Acad. Sci. USA* 95:14628–14633 (1998)).

In another embodiment of the invention, the regulatory polypeptide encoded by the nucleic acid comprises a regulatory domain derived from a kinase, phosphatase or other protein that modifies polypeptides involved in gene regulation. Such modifiers are often involved in switching on or off transcription mediated by, for example, hormones. Kinases involved in transcription regulation are reviewed in Davis, *Mol. Reprod. Dev.* 42:459–67 (1995), Jackson et al, *Adv. Second Messenger Phosphoprotein Res.* 28:279–86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

DNA repair enzymes and their associated factors and modifiers may also provide regulatory domains suitable for use in the transcriptional regulatory polypeptide encoded by the nucleic acid of the present invention. DNA repair systems are reviewed in, for example, Vos, *Curr. Opin. Cell Biol.* 4:385–95 (1992); Sancar, *Ann. Rev. Genet.* 29:69–105 (1995); Lehmann, *Genet. Eng.* 17:1–19 (1995); and Wood,

*Ann. Rev. Biochem.* 65:135–67 (1996). DNA rearrangement enzymes and their associated factors and modifiers can also be used as regulatory domains (see, e.g., Gangloffet al., *Experientia* 50:261–9 (1994); Sadowski, *FASEB J.* 7:760–7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays*, 16:13–22 (1994), and methyltransferases are described in Cheng, *Curr. Opin. Struct. Biol.* 5:4–10 (1995). Chromatin associated proteins and their modifiers (e.g., kinases, acetylases and deacetylases), such as histone deacetylase (Wolffe, *Science* 272:371–2 (1996)) may be useful as domains. In another embodiment, the regulatory domain of the transcriptional regulatory protein is a DNA methyl transferase that acts as a transcriptional repressor (see, e.g., Van den Wyngaert et al., *FEBS Lett.* 426:283–289 (1998); Flynn et al., *J. Mol. Biol.* 279:101–116 (1998); Okano et al., *Nucleic Acids Res.* 26:2536–2540 (1998); and Zardo & Caiafa, *J. Biol. Chem.* 273:16517–16520 (1998)). In still another embodiment, endonucleases such as Fok1 are used as transcriptional repressors, which act via gene cleavage (see, e.g., PCT Publication No. WO 95/09233; and PCT/US94/01201).

In one embodiment of the invention, the transcriptional regulatory polypeptide regulates expression of a diagnostic gene or a therapeutic gene.

B. Cells

The present invention also provides a cell that comprises the nucleic acid molecule of the invention. The cell may be prokaryotic or eukaryotic. In one embodiment, the cell is a mammalian cell. In a preferred embodiment, the cell is a human cell.

In one embodiment, the cell further comprises a second polynucleotide, transcription of which is regulated by the transcriptional regulatory polypeptide encoded by the nucleic acid molecule of the invention. This second polynucleotide is optionally a transgene. The second polypeptide is optionally included in the same nucleic acid molecule as that which produces the transcript bearing the aptamer and the regulatory polypeptide coding sequence. In an alternative embodiment, the second polypeptide is a gene endogenous to the cell.

In a one embodiment, the second polynucleotide, a polynucleotide regulated by the transcriptional regulatory polypeptide, encodes a polypeptide. Preferably, the polypeptide encoded by the second polynucleotide is a therapeutic polypeptide. The therapeutic polypeptide may optionally be selected from the group consisting of a toxin, a cytokine, a kinase, a phosphatase, a transcriptional regulatory protein, an antibody, and a tumor suppressor. In a preferred embodiment, the polypeptide is a tumor suppressor, such as p53.

In an alternative embodiment, the second polynucleotide in the cell yields an antisense RNA molecule upon transcription.

In another embodiment of the invention, the cell further comprises a ligand that binds to the aptamer of the nucleic acid molecule.

C. Expression Cassettes and Preparation of the Nucleic Acids

The nucleic acid molecules are most commonly prepared by in vivo or in vitro transcription from a suitable expression cassette as described below.

The present invention also provides a polynucleotide that encodes a transcriptional regulatory polypeptide and comprises an aptamer sequence. The polynucleotide can be DNA or RNA. The aptamer sequence can be incorporated into, for example, a 5'-untranslated region (5' UTR) in the mRNA transcript or a DNA from which an mRNA transcript is transcribed. The aptamer sequence also can be incorporated into other portions of an mRNA transcript or its corresponding DNA. For example, the aptamer sequence can be present in a region of the transcript that encodes the polypeptide, in which case the aptamer sequence is situated, and its sequence designed, so that the polypeptide is active when expressed. The aptamer sequence can also be positioned in an intron, in which case the presence of the ligand for the aptamer can affect intron splicing. Following transcription of the polynucleotide, the aptamer in the mRNA transcript will, when bound to its ligand, prevent translation of the transcriptional regulatory polypeptide.

Polynucleotides encoding the regulatory polypeptides of this invention can be prepared by any suitable method. For example, nucleic acids encoding a transcriptional regulatory protein or domain can be isolated from a mammalian tissue sample using conventional cloning and/or amplification techniques. A wide variety of cloning and in vitro amplification methods suitable for the construction of the nucleic acid molecules of the invention are well-known to persons of ordinary skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); *Current Protocols in Molecular Biology*, F. M. Ausubel et al, eds., Current Protocols, a joint venture between Greene Publishing Associates, Inc. and John Wiley & Sons, Inc., (1994 Supplement) (Ausubel); Cashion et al., U.S. Pat. No. 5,017, 478; and Carr, European Patent No. 0246864.

Amplification methods such as polymerase chain reaction (PCR) are also useful for preparing the polynucleotides of the invention. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research*, 3:81–94 (1991); Kwoh et al., *Proc. Natl. Acad. Sci. USA* 86:1173 (1989); Guatelli et al., *Proc. Natl. Acad. Sci. USA* 87:1874 (1990); Lomell et al., *J. Clin. Chem* 35:1826 (1989); Landegren et al., *Science* 241:1077–1080 (1988); Van Brunt, *Biotechnology* 8:291–294 (1990); Wu and Wallace, *Gene* 4:560 (1989); and Barringer et al., *Gene* 89:117 (1990).

Alternatively, the polynucleotides encoding the transcriptional regulatory polypeptides can be prepared using known regulatory polypeptide-encoding nucleotide sequences as a guide, with or without sequence optimization, for direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.,* 22:1859–1862 (1981); and the solid support method of U.S. Pat. No. 4,458,066. Oligonucleotide synthesis is typically carried out on commercially available solid phase oligonucleotide synthesis machines (Needham-VanDevanter et al., *Nucleic Acids Res.* 12:6159–6168 (1984)). Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences.

A DNA polynucleotide from which the aptamer will be transcribed will most typically be prepared by using one of the above-mentioned synthetic techniques to generate an oligonucleotide of appropriate sequence. The oligonucleotide will then be amplified using standard PCR technology. The PCR primers used may optionally include restriction sites. Once double-stranded, the PCR amplification product can be cleaved at the restriction site and subsequently ligated upstream of double-stranded DNA containing the sequence encoding the transcriptional regulatory polypeptide.

In one embodiment, nucleic acids of the invention that comprise an aptamer and a polynucleotide that encodes a transcriptional regulatory polypeptide are cloned using DNA amplification methods such as polymerase chain reaction (PCR). Thus, for example, the nucleic acid sequence or subsequence is PCR amplified, using a sense primer containing one restriction site (e.g., NdeI) and the 5' end of the sequence and an antisense primer containing another restriction site (e.g., HindIII) and the 3' end of the sequence. The coding sequence can be examined for the presence of the same restriction sites; if present, they can be mutated to ensure that digestion with the selected enzymes does not cleave the coding sequence. This will produce a DNA molecule which when transcribed will produce an RNA molecule containing an aptamer and encoding the desired transcriptional regulatory polypeptide and having terminal restriction sites. This nucleic acid can then be easily ligated into a vector containing the appropriate corresponding restriction sites. Suitable PCR primers can be determined by one of skill in the art using the known sequence information.

The present invention also provides an expression cassette that comprises a promoter operably linked to a polynucleotide from which is transcribed the nucleic acid molecule of the invention. Preferably, the expression cassette is capable of directing transcription of the nucleic acid molecule of the invention in a desired cell. It is also highly preferred that the expression cassette be capable of directing expression of the regulatory polypeptide in the desired cell in the absence of the aptamer's ligand.

In some embodiments of the invention, the polynucleotide is a transgene that is introduced into a cell. Typically this polynucleotide is carried on an expression vector that includes an expression cassette. The expression cassettes can comprise any promoter which is sufficient for effecting transcription of the aptamer and regulatory polypeptide-encoding region in the desired cellular environment. When introduced into a cell, the promoter drives expression of the gene. The promoter can be constitutively expressed in a particular cell, or can be inducible by a suitable stimulus. The cytomegalovirus (CMV) promoter is one example of a strong constitutive promoter (see, e.g., U.S. Pat. No. 5,168, 062). Tissue specific or inducible promoters find use with the subject invention where it is desired to limit transcription to particular cells, for example proliferating cells or endothelial cells. Examples of promoters include cell-cycle regulated promoters, or those obtained from a cc-interferon gene, a heat shock gene, a metallothionein gene or those obtained from steroid hormone-responsive genes. Such inducible promoters can be used to regulate transcription of a gene by cell cycle status, or by the use of external stimuli such as interferon or glucocorticoids. Since the arrangement of eukaryotic promoter elements is highly flexible, combinations of constitutive and inducible elements also can be used. Tandem arrays of two or more inducible promoter elements can increase the level of induction above levels of transcription achieved when compared to the level of induction achieved with a single inducible element.

Transcriptional enhancer elements are optionally included in the expression cassette. Enhancer DNA sequences are primary regulators of transcriptional activity which can act to increase transcription from a promoter element. Enhancers do not have to be in the 5' orientation with respect to the promoter in order to enhance transcriptional activity, nor do they need to be in the region of the start site of transcription. The combination of promoter and enhancer element(s) used in a particular expression cassette can be selected by one skilled in the art to maximize specific effects. Different enhancer elements can be used to produce a desired level of transgene expression in a wide variety of tissue and cell types. For example, the human CMV immediate early promoter-enhancer element is used to produce high level transgene expression in many different tissues in vivo. Examples of other enhancer elements which confer a high level of transcription on linked genes in a number of different cell types from many species include enhancers from SV40 and RSV-LTR. The SV40 and RSV-LTR are essentially constitutive. They are combined with other enhancers which have specific effects, or the specific enhancers are used alone.

In one embodiment, the control sequences employed in the expression cassette limit expression to only certain types of cells. For instance, if desired, expression can be limited to endothelial cells by using endothelial cell specific promoters and/or enhancers. Such promoters include those obtained from genes of the platelet-derived growth factor/vascular endothelial growth factor (PDGF/VEGF) family, including KDR/flk-1, which controls expression of one of two receptors for vascular endothelial growth factor (Patterson et al., *J. Biol. Chem.* 270:23111–23118 (1995)). Other suitable cell-specific promoters are known to those of skill in the art.

Efficient enhancer elements that are active only in a tissue-, developmental-, or cell-specific fashion are also known. Suitable enhancers include immunoglobulin, CMV, interleukin-2 (IL-2) and β-globin enhancers, as well as those associated with the specifically expressed promoters listed above and others known to those of skill in the art. Alternatively, a tissue-specific promoter can be fused to a very active, heterologous enhancer element, such as the SV40 enhancer, in order to confer both a high level of transcription and tissue-specific transgene transcription. Evaluation of particular combinations of enhancer elements for a particular desired effect or tissue of expression is within the level of skill in the art.

In alternative embodiments of the invention, the gene to be regulated (sans aptamer) is an endogenous gene within an organism. The aptamer is incorporated into, for example, the 5' UTR of an endogenous gene of an organism by the standard techniques of gene targeting known to those of ordinary skill in the art, such as homologous recombination. Suitable methods are described in, for example, U.S. Pat. No. 5,614,396. Thus, the polynucleotide that encodes the regulatory protein can be chromosomal.

D. Vectors

Expression vectors comprising the expression cassettes of the invention are also provided. A number of different types of expression vectors will be apparent to those of ordinary skill in the art. The expression vector is typically chosen to facilitate delivery of the expression cassette into the cell of choice.

In some embodiments of the invention, the vector is nonviral. Nonviral delivery methods include, for example liposome-based gene delivery (Debs and Zhu, PCT Publication No. WO 93/24640 (1993); Mannino and Gould-Fogerite, *BioTechniques* 6(7):682–691 (1988); Rose, U.S. Pat. No. 5,279,833; Brigham, PCT Publication No. WO 91/06309 (1991); and Felgner et al., *Proc. Natl Acad. Sci. USA* 84:7413–7414) (1987).

In other embodiments of the invention, the vector is viral. The viral vector is optionally selected from the group consisting of an adenoviral vector, a retroviral vector, and an adeno-associated viral vector. For instance, replication-defective retroviral vectors harboring a therapeutic polynucleotide sequence as part of the retroviral genome may be used (see, e.g., Miller et al., *Mol. Cell. Biol.* 10:4239 (1990); Kolberg, *J. NIH Res.* 4:43 (1992), and Cornetta et al., *Hum. Gene Ther.* 2:215 (1991)). Widely used retroviral vectors include those based upon Moloney murine leukemia virus (MMuLV), gibbon ape leukemia virus (GaLV), simian immunodeficiency virus (SIV), human immunodeficiency virus (HIV), and combinations thereof. See, e.g., Buchscher et al., *J. Virol.* 66(5):2731–2739 (1992); Johann et al., *J. Virol.* 66(5):1635–1640 (1992); Sommerfelt et al., *Virol.* 176:58–59 (1990); Wilson al., *J. Virol.* 63:2374–2378 (1989); Miller et al., *J. Virol.* 65:2220–2224 (1991); Wong-Staal et al., PCT/US94/05700, and Rosenburg and Fauci, in *Fundamental Immunology, Third Edition* Paul (ed) Raven Press, Ltd., New York (1993) and the references therein, and Yu et al., *Gene Therapy* (1994), supra).

Adenoviral vectors are also commonly used for the introduction of nucleic acids into mammals. See, e.g., Berns et al., *Ann. NY Acad. Sci.* 772:95–104 (1995); Ali et al., *Gene Ther.* 1:367–384 (1994); and Haddada et al., *Curr. Top. Microbiol. Immunol.* 199(3):297–306 (1995) for review.

In one embodiment of the invention, the vector is an adeno-associated virus (AAV). AAVs are single-stranded, replication-defective DNA viruses with a 4.7 kb genome. Adeno-associated viruses are readily obtained, and their use as vectors for gene delivery was described in, for example, Muzyczka, *Curr. Top. Microbiol. Immunol.* 158:97–129 (1992), U.S. Pat. No. 4,797,368, and PCT Publication No. WO 91/18088. Samulski, *Current Opinion in Genetic and Development* 3:74–80 (1993), and the references cited therein, provides an overview of the AAV life cycle. For a general review of AAVs and of the adenovirus or herpes helper functions, see, Bems and Bohensky, *Advances in Virus Research*, Academic Press., 32:243–306 (1987). The genome of AAV is described in Srivastava et al., *J. Virol.,* 45:555–564 (1983). Carter et al., U.S. Pat. No. 4,797,368, describe many of the relevant design considerations for constructing recombinant AAV vectors. See, also, Carter, PCT Publication No. WO 93/24641. Additional references describing AAV vectors include, for example, West et al., *Virology* 160:38–47 (1987); Kotin, *Human Gene Therapy* 5:793–801 (1994); and Muzyczka, *J. Clin. Invest.* 94:1351 (1994). Construction of recombinant AAV vectors is also described in a number of additional publications, including Lebkowski, U.S. Pat. No. 5,173,414; Lebkowski et al., *Mol. Cell. Biol.* 8:3988–3996 (1988); Tratschin et al., *Mol. Cell. Biol.* 5(11):3251–3260 (1985); Tratschin et al., *Mol. Cell. Biol.*, 4:2072–2081 (1984); Hermonat and Muzyczka, *Proc. Natl. Acad. Sci. USA,* 81:6466–6470 (1984); and Samulski et al., *J. Virol.,* 63:03822–3828 (1989). AAV is capable of replicating and forming virus particles only in cells that are also infected with a helper virus. To obtain integration of an AAV genome into a mammalian cell, the cell is infected with the AAV in the absence of a helper virus.

Protocols for in vivo gene therapy using adeno-associated viral vectors have been described for the brain (Alexander et al., *Human Gene Ther.* 7:841–850 (1996)), liver (Koeberl et al., *Proc. Natl. Acad. Sci. USA* 94:1426–1431 (1997)), lung (Flotte et al., *Proc. Natl. Acad. Sci. USA* 90:10613–10617 (1993)), and muscle (Xiao et al., *J. Virol.* 70:8098–8108 (1996)). These methods can be adapted to other target organs by those of ordinary skill in the art.

In one embodiment of the invention, in addition to comprising the expression cassette polynucleotide which produces the aptamer-containing transcript that encodes the transcriptional regulatory polypeptide, the expression vector further comprises a second polynucleotide. Transcription of this second polynucleotide is regulated by the transcriptional regulatory polypeptide. Optionally, the second polynucleotide is operably linked to a binding site for the transcriptional regulatory polypeptide.

In a one embodiment, the second polynucleotide, which is regulated by the transcriptional regulatory polypeptide, encodes a polypeptide. Preferably, the polypeptide encoded by the second polynucleotide is a therapeutic polypeptide.

In an alternative embodiment, the second polynucleotide yields an antisense RNA molecule upon transcription.

E. Methods of Controlling the Expression of Genes

The present invention also provides methods of regulating expression of a gene. The method includes contacting with an aptamer-binding ligand an RNA molecule that comprises both an aptamer and a polynucleotide encoding a transcriptional regulatory polypeptide that regulates expression of the gene. When the ligand binds to the aptamer, translation of the transcriptional regulatory polypeptide is inhibited, resulting in a change in the expression level of the gene.

In a preferred embodiment, the change in the expression level of the gene is proportional to the amount of aptamer-binding ligand administered.

The nature of the gene regulation will depend on the nature of the transcriptional regulatory polypeptide. For instance, in a preferred embodiment, the transcriptional regulatory polypeptide is a repressor. In such an embodiment, binding of the ligand to the aptamer inhibits translation of the repressor, thus causing an increase in the expression level of the gene. In an alternative embodiment, the transcriptional regulatory polypeptide is a transcriptional activator, whereby binding of the ligand to the aptamer inhibits translation of the transcriptional activator, thus causing a decrease in the expression level of the gene.

In some embodiments, the gene whose expression is regulated comprises a binding site for the transcriptional regulatory polypeptide.

One embodiment of the invention is illustrated in FIG. 1. In FIG. 1, a first transcription unit (top) comprises a gene encoding a potent transcription repressor operably linked to a constitutive promoter. Insertion of an aptamer sequence into the 5' untranslated region within the transcription unit facilitates blockage of repressor expression by blocking translation upon addition of ligand. The second transcription unit contains a hybrid promoter (including the repressor binding site) operably linked to a gene of interest. The activity of this hybrid promoter is regulated by the controlled expression of the repressor. The hybrid promoter is not active when the repressor is present, such as in the absence of ligand addition. When ligand is added, the repressor is not expressed. As a result, the hybrid promoter is active and the gene of interest is translated.

The gene whose expression is regulated may optionally be included in a chromosome. Alternatively, the gene may instead be extrachromosomal.

Typically, both the mRNA and the gene whose expression is to be controlled will be in a cell when the contacting of the aptamer with its ligand occurs. The ligand is contacted with the aptamer by administering the ligand to the cell. In a preferred embodiment, the cell is part of a multicellular organism, such as a human. The contacting of the ligand with the aptamer may then be accomplished by administering the ligand to the organism.

In a preferred embodiment of the method, the RNA comprising the aptamer and encoding the transcriptional regulatory polypeptide is transcribed from an expression cassette as described above.

Thus, the present invention provides a method suitable for gene therapy, and, optionally, gene therapy controllable in a dose-responsive manner. For a review of gene therapy procedures, see Anderson, *Science* 256:808–813 (1992); Nabel and Felgner, *TIBTECH* 11:211–217 (1993); Mitani and Caskey, *TIBTECH* 11:162–166 (1993); Mulligan, *Science* 926–932 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer and Perricaudet, *British Medical Bulletin* 51(1):31–44 (1995); Haddada et al. (1995) in *Current Topics in Microbiology and Immunology* Doerfler and Böhm (eds) Springer-Verlag, Heidelberg Germany; and Yu et al., *Gene Therapy* 1:13–26 (1994).

The invention further provides methods of retarding or inhibiting undesirable cell proliferation. These methods include administering to undesirably proliferating cells: (i) a nucleic acid construct that comprises a promoter operably linked to a polynucleotide, where transcription of the polynucleotide yields an mRNA that comprises both an aptamer and a polynucleotide sequence that encodes a transcriptional regulatory polypeptide that regulates expression of a gene involved in regulation of cell proliferation, and (ii) an aptamer-binding ligand that binds to the aptamer. Binding of the ligand to the aptamer inhibits translation of the tranacriptional regulatory polypeptide, thereby causing a change in the expression level of the gene. This change in expression level ameliorates the undesirable cell proliferation.

The polynucleotide whose transcription yields the aptamer-containing RNA that encodes the transcriptional regulatory polypeptide can be either extrachromosomal or chromosomal.

In one presently preferred embodiment, the gene involved in the regulation of cell proliferation is a tumor suppressor gene and the transcriptional regulatory polypeptide is a repressor, so that binding of the ligand to the aptamer results in an increase in the tumor suppressor gene expression level.

In some embodiments, the gene involved in regulation of cell proliferation is a chimeric gene. Optionally, the chimeric gene comprises a promoter operably linked to a polynucleotide that encodes a polypeptide involved in regulation of cell proliferation. The promoter in this embodiment is preferably, but not necessarily, constitutive. The chimeric gene is optionally included on an expression vector that is administered to the undesirably proliferating cells. The nucleic acid construct which codes for the aptamer-containing transcriptional regulatory polypeptide is optionally also included in the same expression vector.

1. Delivery of the Nucleic Acids and Expression Cassettes

For purposes of controlling gene expression, including expression of genes involved in the regulation of cell proliferation, the nucleic acid molecules or expression cassettes of the invention must be administered to cells. Optionally, the expression cassette is part of a larger expression vector which facilitates delivery. Also, in some embodiments as described above, a second polynucleotide which encodes a gene subject to regulation by the transcriptional regulatory polypeptide may be delivered to the same cell or on the same expression vector as the aptamer-producing expression cassette or on a separate expression vector. The therapeutic nucleic acid molecules and expression cassettes of the invention can be administered either in vivo or ex vivo.

a) In Vivo Administration

In one embodiment, a "naked" nucleic acid molecule or expression cassette is introduced directly into a tissue, such as muscle. See, e.g., U.S. Pat. No. 5,580,859. Other methods such as "biolistic" or particle-mediated transformation (see, e.g., Sanford et al., U.S. Pat. No. 4,945,050; U.S. Pat. No. 5,036,006) are also suitable for introduction of anti-angiogenic activity into cells of a mammal according to the invention. These methods are useful not only for in vivo introduction of DNA or RNA into a mammal, but also for ex vivo modification of cells for reintroduction into a mammal. As for other methods of delivering the nucleic acids, if necessary, the administration of the DNA or RNA is repeated in order to maintain the desired level of expression of the transcriptional regulatory polyp eptide.

Vectors (e.g., retroviruses, adenoviruses, liposomes, etc.) containing expression cassettes or nucleic acid molecules of the invention can be administered directly to the organism for transduction of cells in vivo. Administration is optionally by intravenous administration. Administration by direct injection into tissues or by intraperitoneal injection is also suitable, as are other routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

In some embodiments, cells are transfected with plasmid DNA containing the expression cassette of the present invention by cationic lipid mediated gene delivery. For instance, tumor cells can be transfected by such a method. The lipids can be used in formulations for the preparation of lipid vesicles or liposomes for use in gene delivery systems. See Lasic, D., *Liposomes: From Physics to Applications,* Elsevier: Amsterdam, 1993. Typically, cationic lipids are used in combination with a neutral lipid in approximately equimolar amounts.

Cationic lipids of interest include, for example, imidazolinium derivatives (PCT Publication No. WO 95/14380), guanidine derivatives (PCT Publication No. WO 95/14381), phosphatidyl choline derivatives (PCT Publication No. WO 95/35301), and piperazine derivatives (PCT Publication No.

WO 95/14651). Examples of cationic lipids that may be used in the present invention include DOTIM (also called BODAI) (Solodin et al., *Biochem.* 34:13537–13544 (1995)), DDAB (Rose et al., *Bio Techniques* 10(4):520–525 (1991)), DOTMA (U.S. Pat. No. 5,550,289), DOTAP (Eibl and Wooley, *Biophys. Chem.* 10:261–271 (1979)), DMRIE (Felgner et al., *J. Biol. Chem.* 269(4):2550–2561 (1994)), EDMPC (commercially available from Avanti Polar Lipids, Alabaster, Ala.), DC-Chol (Gau and Huang, *Biochem. Biophys. Res. Comm.* 179:280–285 (1991)), DOGS (Behr et al., *Proc. Natl. Acad. Sci. USA,* 86:6982–6986 (1989)), MBOP (also called MeBOP) (PCT Publication No. WO 95/14651), and those described in PCT Publication No. WO 97/00241. In addition, cationic lipid carriers having more than one cationic lipid species may be used to produce complexes for delivery of the expression cassettes or nucleic acid molecules of the invention.

Neutral lipids of use in transfection complexes include, for example, dioleoyl phosphatidylethanolamine (DOPE), Hui et al., *Biophys. J.* (71)590–599 (1996); cholesterol, Liu et al., *Nat. Biotech.* 15:167–173 (1997).

The lipid mixtures typically are prepared in chloroform, dried, and rehydrated in, e.g., 5% dextrose in water or a physiologic buffer to form liposomes. Liposomes may be LUVs, MLVs, or SUVs. Usually, the liposomes formed upon rehydration are predominantly MLVs, and SUVs are formed from them by sonication or by extrusion through membranes with pore sizes ranging from 50 to 600 nm to reduce their size. The resulting liposomes are mixed with a nucleic acid solution with constant agitation to form the cationic lipid-nucleic acid transfection complexes. Preferred transfection complex size for intravenous administration is from 50 to 5000 nm, most preferably from 100 to 400 nm.

Preferably, DNA/lipid complexes are prepared at a DNA concentration of about 0.625 mg/ml. The dose delivered is from about 10 $\mu$g to about 2 mg per gram of body weight. Repeat doses may be delivered at intervals of from about 2 days to about 2 months, as necessary.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

The dose administered to a patient, in the context of the present invention should be sufficient to effect a beneficial therapeutic response in the patient over time. The dose will be determined by the efficacy of the particular vector employed and the condition of the patient, as well as the body weight or vascular surface area of the patient to be treated. The size of the dose also will be determined by the existence, nature, and extent of any adverse side-effects that accompany the administration of a particular vector, or transduced cell type in a particular patient.

In determining the effective amount of the vector to be administered to modulated gene expression, the physician evaluates vector toxicities, progression of the disease, and the production of anti-vector antibodies, if any. In general, the dose equivalent of a naked nucleic acid from a vector is from about 1 $\mu$g to 1 mg for a typical 70 kilogram patient, and doses of vectors used to deliver the nucleic acid are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

b) Ex Vivo Administration

The methods of the invention are useful for ex vivo applications, in which cells are removed from an organism, genetically modified using the methods, and reintroduced into an organism. In some applications genetically modified cultured cell lines will be introduced into an organism. The genetically modified cells can be introduced into the same organism from which the cells were originally obtained, or can be introduced into a different organism of the same or a different species. Ex vivo therapy is useful, for example, in treating genetic diseases such as hemophilia and certain types of thalassemia, as well as other diseases that are characterized by a defect in a cell that can be removed from the animal, modified using the methods of the invention, and reintroduced into the organism. The cells can be, for example, hematopoietic stem cells, which are derived from bone marrow or fetal cord blood, T-lymphocytes, B-lymphocytes, monocytes, liver cells, muscle cells, fibroblasts, stromal cells, skin cells, or stem cells. The cells can be cultured from a patient, or can be those stored in a cell bank (e.g., a blood bank). These methods are useful for treating humans, and also for veterinary purposes.

The modified cells are administered to the animal or patient at a rate determined by the $LD_{50}$ of modified cell type, and the side-effects of cell type at various concentrations, as applied to the mass and overall health of the patient. Administration can be accomplished via single or divided doses.

Animal models and clinical protocols for ex vivo gene therapy have been established for hematopoietic cells (Blaese et al., *Science* 270:475–480 (1995); Kohn et al., *Nature Med.* 1:1017–1023 (1995)), liver cells (Grossman et al., *Nature Genet.* 6:335–341 (1994)), muscle cells (Bonham et al., *Human Gene Ther.* 7:1423–1429 (1996)), skin cells (Choate et al., *Nature Med.* 2:1263–1267 (1996)) and fibroblasts (Palmer et al., *Blood* 73:438–445 (1989)).

2. Pharmaceutical Compositions of Ligands

The ligand bound by the aptamer which inhibits translation must be administered to an organism when it is desirable to turn off expression of the transcriptional regulatory polypeptide. The ligand is preferably administered to an organism as a pharmaceutical composition. Generally, either the ligand pharmaceutical composition will be administered to cells where the aptamer-containing transcripts which encode transcriptional regulatory proteins are already present in the cells or the ligand pharmaceutical composition will be administered to the cells at the same time as the nucleic acid molecules or expression cassettes of the invention.

The aptamer ligands may be formulated as pharmaceutical compositions for parenteral (e.g., subcutaneous, intramuscular, intradermal, or intravenous), topical, oral, rectal, intrathecal, buccal (e.g., sublingual), or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the some ligands, when administered orally, must be protected from digestion. This is typically accomplished either by complexing the ligand with a composition to render it resistant to acidic and enzymatic hydrolysis or by packaging the protein in an appropriately resistant carrier such as a liposome. The ligand may also be provided in a formulation that provides for slow release of the active ingredient.

The ligand pharmaceutical compositions may be useful for topical administration or for parenteral administration, such as intravenous administration or administration into a body cavity or lumen of an organ. The compositions for administration will commonly comprise a solution of the ligand dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of ligand in these formulations can vary widely, and will be selected primarily based on fluid volumes, viscosities, body weight and the like in accordance with the particular mode of administration selected and the patient's needs.

In therapeutic applications, compositions are administered to a patient suffering from a disease (e.g., a cancer or other disease that is associated with undesirable gene expression) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

The toxicity and therapeutic efficacy of the ligand is determined using standard pharmaceutical procedures in cell cultures or experimental animals. One can determine the $LD_{50}$ (the dose lethal to 50% of the population) and the $ED_{50}$ (the dose therapeutically effective in 50% of the population) using procedures presented herein and those otherwise known to those of skill in the art. For example, anti-cell proliferation activity can be assayed as described by Mosmann, T. (1983) *J. Immunol. Meth.* 65:55–63 and Skehan et al. (1990) *J. Nat'l. Cancer Inst.* 82:1107–1112. Antimetastasis and antitumor activity can be determined by the ability of a treatment to reduce the size and number of tumor colonies in vivo (Tuszynski et al. (1987) *Cancer Research* 47:4130–4133).

The therapeutic index ($LD_{50}/ED_{50}$) can be determined from these experiments. Dosages are typically employed that result in a circulating concentration that results in little or no toxicity and includes the $ED_{50}$. The dosage may vary within this range depending upon the dosage form employed and the route of administration utilized. One can use animal models to determine appropriate dosages which result in effective disruption of expression of the targeted transcriptional regulatory protein.

A typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The invention also provides packs, dispenser devices, and kits for administering gene regulation activity to a manimal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a tumor, or for preventing or treating other diseases or conditions that are associated with undesirable levels of gene expression.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An expression vector that comprises an expression cassette, wherein said cassette comprises a promoter operably linked to a polynucleotide from which is transcribed a nucleic acid; and wherein said nucleic acid molecule comprises an aptamer and a polynucleotide that encodes a transcriptional regulatory polypeptide, and wherein binding of a ligand to said aptamer inhibits translation of said transcriptional regulatory polypeptide; and wherein said expression vector further comprises a second polynucleotide, wherein transcription of said second polynucleotide is regulated by said transcriptional regulatory polypeptide.

2. The expression vector of claim 1, wherein the second polynucleotide encodes a therapeutic polypeptide.

3. The expression vector of claim 1, wherein the second polynucleotide is operably linked to a binding site for the transcriptional regulatory polypeptide.

4. The expression vector of claim 1, wherein the ligand is a cell-permeable small organic molecule.

5. The expression vector of claim 4, wherein the ligand is Hoechst dye 33258.

6. The expression vector of claim 1, wherein the ligand is a metal ion.

7. The expression vector of claim 1, wherein the ligand is an antibiotic.

8. The expression vector of claim 1, wherein the ligand is a steroid.

9. The expression vector of claim 1, wherein the transcriptional regulatory polypeptide is a repressor.

10. The expression vector of claim 1, wherein the transcriptional regulatory polypeptide is a transcriptional activator.

11. The expression vector of claim 1, wherein the transcriptional regulatory polypeptide is a coactivator.

12. The expression vector of claim 1, wherein the transcriptional regulatory polypeptide comprises a DNA-binding domain.

13. The expression vector of claim 12, wherein the DNA-binding domain is that of a protein selected from the group consisting of E2F-1, GAL4, a STAT ("Signal Transducer and Activator of Transcription") protein, a steroid/thyroid receptor protein, a Cys2-His2 zinc finger DNA binding motif, and a tetracycline repressor.

14. The expression vector of claim 1, wherein the transcriptional regulatory polypeptide comprises a transcriptional repressor domain.

15. The expression vector of claim 14, wherein the transcriptional repressor domain is that of a protein selected from the group consisting of Rb protein, v-erbA, retinoic acid receptor alpha, thyroid hormone receptor alpha, yeast Ssn6/Tup1 protein complex, SIR1, NeP1, TSF3, SFI, WT1, Oct-2.1, E4BP4, KRAB and ZF5.

16. The expression vector of claim 14, wherein the transcriptional repressor domain is that of p53.

17. The expression vector of claim 1, wherein the transcriptional regulatory polypeptide comprises a transcriptional activation domain.

18. The expression vector of claim 1, wherein the expression vector is a viral vector.

19. The expression vector of claim 1, wherein the viral vector is selected from the group consisting of an adenoviral vector, a retroviral vector, and an adeno-associated viral vector.

20. The expression vector of claim 1, wherein the expression vector is a nonviral vector.

21. An isolated cell comprising a nucleic acid molecule, wherein said nucleic acid molecule comprises an aptamer and a polynucleotide that encodes a transcriptional regulatory polypeptide; and wherein binding of a ligand to the aptamer inhibits translation of said transcriptional regulatory polypeptide; and wherein said cell further comprises a second polynucleotide, wherein transcription of said second polynucleotide is regulated by said transcriptional regulatory polypeptide.

22. The cell of claim 21, wherein the second polynucleotide is included in the nucleic arid.

23. The cell of claim 21, wherein transcription of the second polynucleotide yields an antisense nucleic acid.

24. The cell of claim 21, wherein the second polynucleotide encodes a polypeptide.

25. The cell of claim 21, wherein the polypeptide is a therapeutic polypeptide.

26. The cell of claim 21, wherein the therapeutic polypeptide is selected from the group consisting of a toxin, a cytokine, a kinase, a phosphatase, a transcriptional regulatory protein, an antibody, and a tumor suppressor.

27. The cell of claim 21, wherein the polyp eptide is a tumor suppressor.

28. The cell of claim 21, wherein the tumor suppressor is p53.

* * * * *